United States Patent
Schaedlich et al.

(10) Patent No.: US 7,713,742 B2
(45) Date of Patent: May 11, 2010

(54) CALIBRATION GAS DELIVERY APPARATUS

(75) Inventors: Frank R. Schaedlich, Toronto (CA); Daniel R. Schneeberger, Scarborough (CA)

(73) Assignee: Tekran Instruments Corporation, Halifax (CA)

( * ) Notice: Subject to any disclaimer, the term of this patent is extended or adjusted under 35 U.S.C. 154(b) by 782 days.

(21) Appl. No.: 11/345,658

(22) Filed: Feb. 2, 2006

(65) Prior Publication Data
US 2007/0178015 A1 Aug. 2, 2007

(51) Int. Cl.
*G01N 33/00* (2006.01)
*G01N 31/00* (2006.01)
*G01N 35/00* (2006.01)
*B01L 3/02* (2006.01)
*G01J 3/30* (2006.01)

(52) U.S. Cl. ............... 436/9; 422/100; 422/68.1; 422/83; 436/18; 73/1.03

(58) Field of Classification Search ............... 436/9, 436/18; 422/100, 68.1, 83; 356/316; 73/1.03
See application file for complete search history.

(56) References Cited

U.S. PATENT DOCUMENTS

| | | | | |
|---|---|---|---|---|
| 3,890,100 | A * | 6/1975 | Busch | 436/136 |
| 4,254,797 | A | 3/1981 | Mayeaux | |
| 4,474,048 | A | 10/1984 | Schmidt | |
| 4,541,966 | A * | 9/1985 | Smith | 261/27 |
| 5,147,612 | A | 9/1992 | Raal | |
| 5,394,730 | A | 3/1995 | Crozier et al. | |
| 5,493,891 | A | 2/1996 | Slemeyer | |
| 5,620,524 | A * | 4/1997 | Fan et al. | 118/726 |
| 5,731,508 | A | 3/1998 | Slemeyer | |
| 5,879,948 | A * | 3/1999 | Van Pelt et al. | 436/81 |
| 6,234,001 | B1 | 5/2001 | Sorensen et al. | |
| 6,475,802 | B2 | 8/2001 | Schaedlich et al. | |
| 6,761,056 | B2 | 7/2004 | Schram et al. | |
| 6,830,730 | B2 * | 12/2004 | Rhodes | 422/78 |

(Continued)

OTHER PUBLICATIONS

IAS GMBH, "Hovacal Hot-Vapor-Calibration", Operating Instructions, Jan. 2004, pp. 1-28.

(Continued)

*Primary Examiner*—Lyle A Alexander
*Assistant Examiner*—Dean Kwak
(74) *Attorney, Agent, or Firm*—Bereskin & Parr LLP; H. Samuel Frost

(57) ABSTRACT

A calibration gas generation method and apparatus for generating a selectively humidified calibration gas to a measurement probe includes a delivery conduit having a conduit inlet adapted to receive a carrier gas stream and a conduit outlet for delivering a calibration gas stream. The apparatus is provided with a first injection unit having a first intake in fluid communication with a first reservoir and a first outlet in fluid communication with the delivery conduit, the first reservoir being adapted to hold a first analyte in liquid form, and a second injection unit having a second intake in fluid communication with a second reservoir and a second outlet in fluid communication with the delivery conduit, the second reservoir being adapted to hold a humidificant in liquid form. The apparatus further includes at least one vaporizer downstream of the first and second outlets and upstream of the conduit outlet for converting the analyte and humidificant liquids to vapor form and delivering a calibration gas including the carrier gas, analyte vapor, and humidificant vapor to the conduit outlet.

12 Claims, 3 Drawing Sheets

U.S. PATENT DOCUMENTS

| | | |
|---|---|---|
| 6,852,542 B2 | 2/2005 | Mandel et al. |
| 7,454,945 B1 * | 11/2008 | Kita et al. ................... 73/1.03 |
| 2004/0152198 A1 | 8/2004 | Mandel et al. |

OTHER PUBLICATIONS

IAS GMBH, "Hovacal digital MF", Preliminary Data Sheets, Apr. 2005, pp. 1-5.

IAS GMBH, "Hovacal Hot-Vapor-Calibration".

ECHCHEM Analytics, "Quotation #26901HOVACAL" dated Jan. 16, 2006, Hovacal B (Basic) Hot Vapor Calibration, Customer; Sales Call Consulting, pp. 1-4.

Tekran Inc., "Model 3310—Mercury CEM Calibration Unit", Apr. 2005, pp. 1-2.

Peter Wilbring, et al., "A Portable Calibration Gas Generator for H20, HC1, NH3 and Mercury", CEM 2001, International Conference on Emissions Monitoring, Apr. 25-27, 2001, Arnheim, Netherlands.

Tekran Instruments Corporation, "Model 3315—Ionic Mercury Calibration Unit", Oct. 2006.

Interim EPA Traceability Protocol for Qualification and Certification of Oxidized Mercury Gas Generators *Deliberative Draft, Revision 2* Apr. 10, 2009.

* cited by examiner

CALIBRATION GAS DELIVERY APPARATUS

FIELD

This invention relates to an apparatus and method for providing a calibration gas to, for example, a continuous emissions monitoring device.

INTRODUCTION

Calibration of gas monitoring systems is generally a mandatory procedure in the maintenance of gas monitoring systems to ensure that accurate readings from the systems are being obtained. It is common practice to introduce a known concentration of the analyte in an inert gas or in a zero air matrix to calibrate a gas monitoring system.

An example of a gas monitoring system is a continuous emissions monitor (CEM) used to monitor the amount of mercury discharged in smoke stacks of power generation installations or incinerators. To ensure that the CEM system is operating satisfactorily, a calibration routine is periodically performed in which the discharged gas normally being monitored is replaced with a calibration gas containing a known amount of mercury. The mercury level indicated by the CEM is then compared to the known amount contained in the calibration gas, and corrective action can be taken where any unacceptable deviation is found. The calibration procedure must typically conform to government standards (e.g. US EPA (Environmental Protection Agency)), and in the case of mercury CEM systems, both elemental and halogenated mercury standard gasses may need to be accommodated for calibration.

Various apparatus and methods for calibration of mercury gas monitoring systems are known. Elemental mercury at low volumetric concentrations may be provided in cylinders (Spectra Gases). Each of such prepared cylinders must be compared against a certified standard in order to have a concentration value assigned to it. These cylinders are expensive, and thus are not economical to generate the high volumes of gas required for the calibration of most analytical systems. Generally all of the mercury CEM systems that are currently available employ an inertial filter arrangement. To calibrate through this type of filter, a very large sample flow of calibration gas, typically in excess of 20 l/m, is required.

Calibrators which generate elemental mercury with a saturated mercury vapor chamber, such as Tekran® Model 3310 Elemental Mercury Calibrator, are known. Calibrators of this type rely on first principles. The vapor pressure of elemental mercury is a well-characterized function of temperature. A known gas flow is first passed through a chamber containing liquid mercury. By saturating the gas with mercury vapor, the gas exits the chamber in equilibrium at the prescribed chamber temperature. A second known gas flow is then used to dilute the saturated gas stream. This method will produce known concentrations if the temperature of the source, chamber flow rate and dilution gas flow rate are known. These variables are easily measured in a manner that is traceable to standards set by NIST (National Institute of Science and Technology). Saturated sources can generate large volumes of elemental calibration gases over a wide range of concentrations at little cost.

Permeating devices may also be used for the generation of elemental mercury. At high emission rates, permeation devices may be certified gravimetrically. At low levels, gravimetric certification is not practical so the sources must be calibrated against some other primary standard.

In U.S. Pat. No. 6,852,542 (Mandel et al.), a method and system for creating a mercury halide standard for use in testing a mercury analyzer system is disclosed. This system uses a known reaction for producing mercury chloride. A known amount of elemental mercury and a gaseous stream containing chlorine are fed to a reaction chamber to form mercury halide. The mercury halide is then fed to a mercury analyzer system where it is converted to form gaseous elemental mercury which is then measured by a mercury analyzer. Comparing either the amount of elemental mercury supplied to the reaction chamber or the amount of mercury halide formed in the reaction chamber with the amount of elemental mercury converted from the mercury halide, the conversion of mercury halide to gaseous elemental mercury by the mercury analyzer system can be evaluated. In practice, the rate of conversion from elemental mercury to mercury chloride is problematical.

In U.S. Pat. No. 6,475,802 (Schaedlich et al.), a method and apparatus for collecting a sample of gaseous mercury and to differentiate between the different gaseous mercury components is disclosed. A quartz denuder module is provided having a coated extended surface for adsorbing reactive gaseous mercury. After collection of a sample, the coating is heated to desorb the mercury as elemental gaseous mercury, which can then be detected and measured in a conventional analyzer. This device may be calibrated using any type of device capable of producing sufficiently low levels. Other patents and applications to the same inventors and relating to mercury detection are U.S. Pat. Nos. 5,597,535, 5,660,795 and 6,475,802 and U.S. patent application Ser. Nos. 10/931,987 and 11/086,480, all of which are hereby incorporated by reference.

In another calibration gas generator marketed under the brand name Hovacal™, a dilute mercury solution is pumped to a vaporizer by a peristaltic pump. The solution is weighed over time using a precision balance to determine the rate of use. A known gas flow is used to dilute the mercury vapor to a known concentration.

There are problems with these known approaches. Most of the systems described above produce a dry calibration gas. Mercury chloride does not travel well in a dry gas, resulting in sample transport problems and lengthy equilibration times. A more severe problem is the poor transport of all mercury compounds, including elemental mercury, through the front end CEM components, including the probe and filter components. In practice, QA/QC techniques such as standard additions may show that a continuous mercury analyzer (CEM) is operating properly when confronted with the normal stack gas matrix being monitored. However, when confronted with the radically different matrix of a typical calibration gas, these components will often fail to transport the calibration gas properly until they reach equilibrium with the new gas. This can result in very lengthy calibration times which do not meet regulatory requirements. In cases where the coal produces a particularly reactive fly ash, the losses when using a dry calibration gas are consistent until the probe is mechanically cleaned. This can occur even when using inertial separator filters rather than conventional filters.

The Hovacal is a system that generates humidified gas, however, it is manual in operation. It has a single, manually controlled injection port and cannot automatically generate various concentrations of analyte while retaining, for example, a constant water concentration in the gas without continually changing solutions, i.e. the water or vapor concentration in the gas inherently depends on the concentration of the analyte in the solution and the rate at which the solution is added to the gas flow. To change the vapor concentration different supplies of the analyte solution with different concentrations are needed.

SUMMARY

The present invention provides an apparatus and method for generating a calibration gas for a gas monitoring system, that is simple and economical and may be fully automated. It provides accurate, reproducible, and stable calibration gas with the capability to be transported through analytical instrumentation systems. The present invention can also provide an apparatus and method that is effective in generating a wide variety of different calibration gas compositions such that multi-point calibrations may be provided and that the gas can continue to emulate the composition of the actual flue gas being monitored as the analyte concentration is varied.

According to one aspect of the invention, a calibration gas delivery apparatus for delivering a selectively humidified calibration gas to a measurement probe is provided. The apparatus includes a delivery conduit having a conduit inlet adapted to receive a carrier gas stream and a conduit outlet for delivering a calibration gas stream. The apparatus is provided with a first injection unit having a first intake in fluid communication with a first reservoir and a first outlet in fluid communication with the delivery conduit, the first reservoir being adapted to hold a first analyte in liquid form, and a second injection unit having a second intake in fluid communication with a second reservoir and a second outlet in fluid communication with the delivery conduit, the second reservoir being adapted to hold a humidificant in liquid form. The apparatus further includes at least one vaporizer downstream of the first and second outlets and upstream of the conduit outlet for converting the analyte and humidificant liquids to vapor form and delivering a calibration gas including the carrier gas, analyte vapor, and humidificant vapor to the conduit outlet.

In accordance with a first aspect of the present invention, there is provided a calibration gas delivery apparatus for delivering a selectively humidified calibration gas to a measurement probe, the apparatus comprising:

a) a delivery conduit having a conduit inlet adapted to receive a carrier gas stream and a conduit outlet for delivering a calibration gas stream;

b) a first injection unit having a first intake in fluid communication with a first reservoir and a first outlet in fluid communication with the delivery conduit, the first reservoir adapted to hold a first analyte in liquid form;

c) a second injection unit having a second intake in fluid communication with a second reservoir and a second outlet in fluid communication with the delivery conduit, the second reservoir adapted to hold a humidificant in liquid form; and d) at least one vaporizer downstream of the first and second outlets and upstream of the conduit outlet for converting the analyte and humidificant liquids to vapor form and delivering a calibration gas including the carrier gas, analyte vapor, and humidificant vapor to the conduit outlet.

In accordance with another aspect of the present invention, there is provided a calibration gas delivery apparatus for delivering a selectively humidified calibration gas to a measurement probe, the apparatus comprising:

a) a delivery conduit having a conduit inlet adapted to receive at least one carrier gas stream including an analyte and a conduit outlet for delivering a calibration gas stream;

b) an injection unit having an intake in fluid communication with a reservoir and an outlet in fluid communication with the delivery conduit, the reservoir adapted to hold a humidificant in liquid form; and c) at least one vaporizer downstream of the conduit outlet and upstream of the conduit outlet for converting the humidificant to vapor form and delivering a calibration gas including all of said at least one carrier gas, and humidificant vapor to the conduit outlet.

In accordance with a further aspect of the present invention, there is provided a method of generating a calibration gas including at least one analyte and at least one humidificant, the method comprising:

a) supplying at least one carrier gas;

b) providing the carrier gas with at least one analyte, each analyte being provided at known concentration in the carrier gas;

c) adding humidity to the carrier gas flow, to give a desired humidity level; and d) supplying the carrier gas including the analyte and added humidity to measuring equipment for detecting the analyte to enable calibration of the measuring equipment.

BRIEF DESCRIPTION OF THE DRAWINGS

For a better understanding of the present invention and to show more clearly how it would be carried into effect, reference will now be made by way of example, to the accompanying drawings that show embodiments of the present invention, and in which.

DESCRIPTION OF EMBODIMENTS OF THE INVENTION

Aspects of the present invention and applicants' teachings may be further understood in light of the following examples, which should not be construed as limiting the scope of the present teachings in any way.

Figure 1:
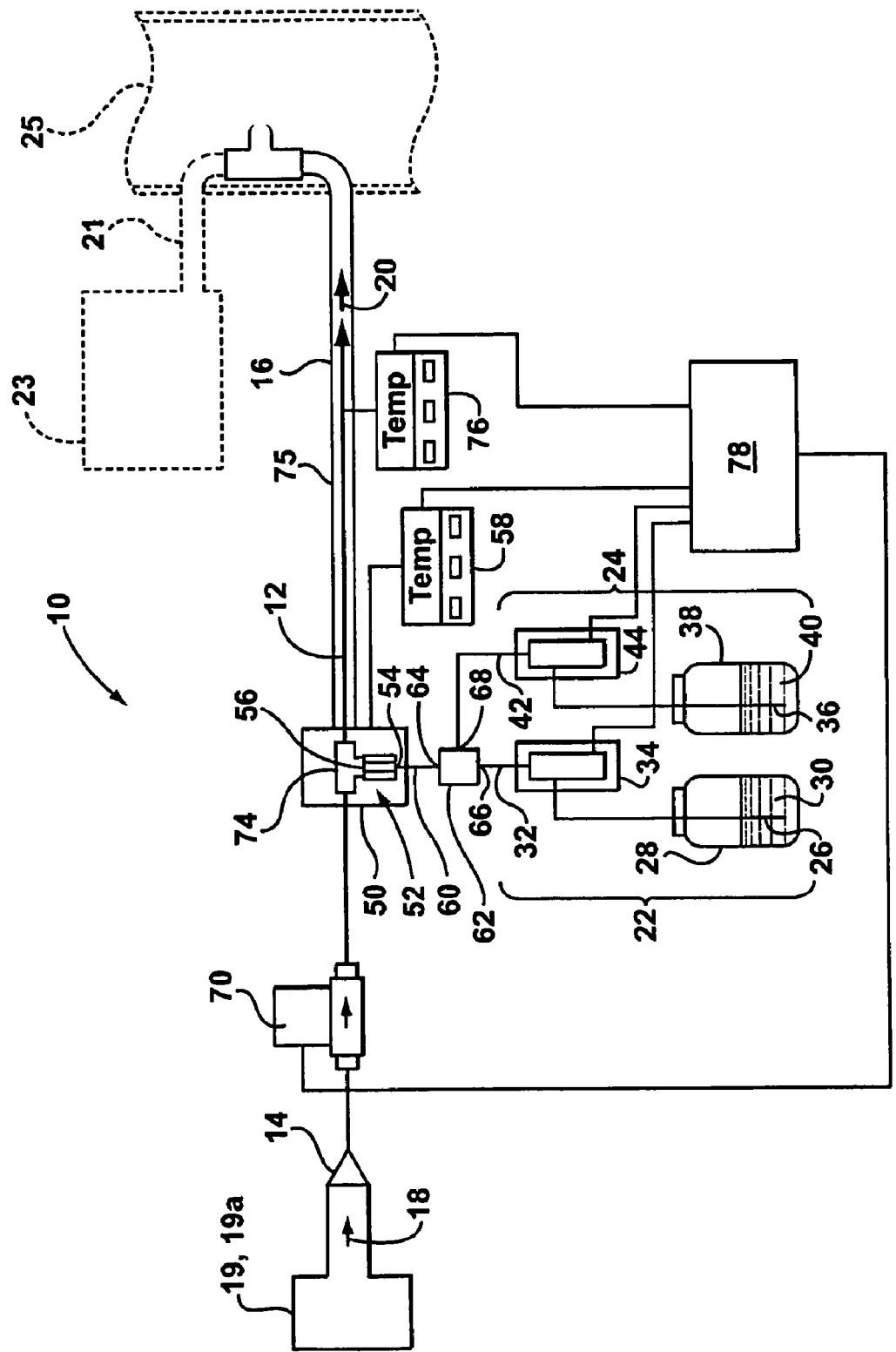
FIG. 1 is a schematic diagram of an embodiment of a calibration gas delivery apparatus in accordance with the present invention.

A calibration gas delivery apparatus 10 in accordance with the present invention is shown in FIG. 1. The apparatus 10 includes a delivery conduit 12 having a conduit inlet 14 and a conduit outlet 16 between which the conduit 12 is adapted to convey fluids.

The inlet 14 is, in the embodiment illustrated, adapted to receive a carrier gas stream 18, which can be provided from a carrier gas source 19. The outlet 16 provides delivery of a calibration gas 20. The calibration gas 20 can provide a known level of a component being measured to a measurement probe 21 for comparison against the level indicated by an associated measurement device 23. In FIG. 1, the probe 21 is schematically shown within an emissions stack 25.

Usually, the outlet 16 is connected to the sample probe 21 by a T connector as shown. The stem of the T extends into the emissions stack for collection of a sample of the emission or flue gas in normal operation. The stem is usually short.

The apparatus 10 includes a first injection unit 22 and a second injection unit 24 for introducing respective components into the delivery conduit 12.

In the embodiment illustrated, the first injection unit 22 has a first intake 26 located within a first reservoir 28. The first reservoir 28 contains a supply of an analyte 30. The analyte 30 is generally defined by the component to be measured by the measurement device 23 to which the calibration gas 20 is being supplied. In the embodiment illustrated, the analyte 30 can be in the form of a liquid mercury chloride, or other ionic mercury solution, and the calibration gas 20 can be supplied to a mercury continuous emission monitoring system.

The first injection unit 22 has a first outlet 32 in fluid communication with the delivery conduit 12. To provide flow of the analyte 30 from the first intake 26 to the first outlet 32, the first injection unit 22 can be provided with a first flow inducer 34. The first flow inducer 34 can include a precise automated liquid delivery mechanism, such as, for example, but not limited to, a calibrated piston displacement pump. The flow inducer can thus deliver a known volume of the analyte 30 to the delivery conduit 12, to provide a known flow rate of iconic mercury, to provide a known flow rate of ionic mercury.

The second injection unit 24 has a second intake 36 in fluid communication with a second reservoir 38. The second reservoir 38 contains a supply of humidificant 40, and is also referred to herein as "humidifier reservoir" 38. In the embodiment illustrated, the humidificant 40 may be in the form of deionized liquid water, but for some applications, the humidificant can comprise water containing a mixture of one or more dilute acids.

The second injection unit 24 has a second outlet 42 in fluid communication with the delivery conduit 12. To facilitate flow of the water 40 from the second intake 36 to the second outlet 42, the second injection unit 24 can be provided with a second flow inducer 44. In the embodiment illustrated, the flow inducer 44 is in the form of a calibrated piston displacement pump, similar to, or the same as, the first flow inducer 34. The second injection unit 24, in the embodiment illustrated, can selectively deliver known amounts of the humidificant 40 to the delivery conduit 12 over a wide range of volumes and known flow rates. Levels or flow rates may, by way of example, be in the range 0.01 to 5 ml/min. This allows selective humidification of the calibration gas 20 to generally any desired level of water concentration.

The calibration gas 20, in the embodiment illustrated, is delivered to the measurement probe in vapor phase. To convert the liquid phase analytes 30 and 40 of the illustrated embodiment into vapor phase, the apparatus 10 is provided with a vaporizer 50. The vaporizer 50 generally provides a heated flow path 52 that has an upstream end 54 in fluid communication with the first and second outlets 32 and 42 of the first and second injection units 22, 24, and a downstream end 56 in fluid communication with the delivery conduit outlet 16. The liquid analyte 30 and water 40 delivered by the first and second injection units 22 and 24 is directed through the heated flow path 52 of the vaporizer 50, where it is converted to vapor phase. The temperature of the heated flow path 52 can be controlled by a vaporizer temperature controller 58.

In the illustrated embodiment of the apparatus 10, both the analyte 30 and water 40 are consumed from respective sources in the same phase (i.e. the liquid phase). Therefore, the delivery of the analyte 30 and water 40 can be controlled (metered) independently using the same principles (e.g. displacement of the generally non-compressible liquids in a positive displacement pump). In the liquid phase and at constant temperatures, they can be treated as incompressible (and in any event need not be subject to any excess pressures) so the mass flow rates are readily determined from volume flow rates.

Furthermore, supplying the components (e.g. the analyte 30) for introduction into the carrier gas 18 in liquid form allows introduction of some analytes that cannot readily be supplied in gaseous form, for example mercury chloride. As well, at least for some analytes, the analyte stored in liquid form can be more stable over time than the corresponding vapor form. Stabilizing agents, such as, for example, but not limited to, weak acids can be added to the liquid analyte 30 in the analyte reservoir 28 to further enhance the stability of the analyte. As detailed below, the presence of stabilizing acids is an additional humidificant that can help to simulate the gas conditions present in normal use.

In the embodiment illustrated, the vaporizer 50 receives a combined liquid flow 60 at its upstream end 54 that includes a mixture of the analyte 30 and the humidificant 40. The apparatus 10, in the embodiment illustrated, is provided with a manifold 62 having an exhaust port 64 for discharging the combined liquid flow 60 to the upstream end 54 of the vaporizer 50. The manifold 62 has first and second inlet ports 66 and 68 that are connected for fluid communication with the first and second outlets 32 and 42, respectively, of the first and second injection units 22 and 24, respectively.

In use, the carrier gas 18 is directed into the inlet 14 of the delivery conduit 12. The carrier gas 18 can be a zero gas, such as air or nitrogen, for generating a "zero" reading on the measurement device 23. The carrier gas 18 is generally dry (free of any water vapor). The supply rate of the carrier gas 18 to the delivery conduit 12 can be controlled and measured by a mass flow controller 70 located adjacent the inlet 14 of the delivery conduit 12.

The liquid analyte 30 and humidificant 40 can be pumped from the respective reservoirs 28 and 38, and fed to the vaporizer 50 for conversion from the liquid phase to the vapor phase, forming a mixed component gas 72 at the downstream end 56 of the heated flow path 52. The mixed component gas 72 (i.e. water vapor and analyte vapor mixture) can then be fed into the delivery conduit 12 via a T-fitting 74. The T-fitting 74 connects the downstream end 56 of the flow path 52 to the delivery conduit 12.

Downstream from the T-fitting, the conduit comprises a chemically inert delivery line, optionally provided with a heater 75, to ensure that analytes and humidificants do not condense onto the walls of the line. Whether a heater is required will depend on a number of factors such as: nature and vapor pressures of the analytes and humidificants at the prevailing temperatures; their concentrations in the gas flow Downstream of the T-fitting 74, the mixed component gas 72 mixes with the carrier gas 18 to form the calibration gas 20. The calibration gas 20 can include an amount of the analyte 30 in vapor form, the concentration of which can be controlled by adjusting the rate at which the first flow inducer 34 provides the liquid analyte 30 to the first injection outlet 32. For example, where the first flow inducer 34 includes a positive displacement pump, the number of rotations of the pump per unit time can be increased or decreased to adjust the relative concentration of the vapor analyte 30 per unit volume of the calibration gas 20.

Similarly, the calibration gas 20 can include an amount of a humidificant, such as water 40, in vapor form, the concentration of which can be adjusted by adjusting the rate at which the second flow inducer 44 provides the liquid humidificant 40 to the second injection outlet 42.

The apparatus 10 can be used to supply a calibration gas 20 that has a precisely known amount of components or chemicals to be measured. The calibration gas 20 can contain a precisely known amount of water vapor to humidify the calibration gas 20. Humidification of the calibration gas 20 can facilitate the transport of the analyte through the probe 21 and other CEM components 23 even after the surfaces have been coated by reactive fly ash deposits. Humidification should be such as to simulate the conditions present during normal operation and sample testing. The present inventors have realized that, if this is done, then any built up fly ash or other contaminants will, it is believed, behave in essentially the same way as they do when normal stack gases etc. are passing through. In particular it is believed that with the calibration gas humidified to simulate the usual sample gas, mercury or other components of interest will not tend to be adsorbed by the fly ash. Humidification of the calibration gas 20 can also facilitate prevention of species conversion of the mercury (for example, oxidation of the mercury) by enabling members of the measurement/calibration system, such as, for example, the probe 21, to operate at cooler temperatures.

The apparatus 10 can be provided with an electronic controller 78 for controlling and/or monitoring one or more of the first flow inducer 34, the second flow inducer 44, the vaporizer temperature controller 58, the mass flow controller 70 and the temperature controller for the downstream portion of the delivery conduit 12. The electronic controller 78 can be programmed to automatically adjust the amounts of analyte 30 and water 40 being supplied to the delivery conduit 12 for changing the respective concentrations in the calibration gas 20, thereby facilitating multi-point automatic calibration of the measurement device 23. The electronic controller 78 (or a separate, second controller in communication with the controller 78) can calculate the concentration and total delivery rate of the analyte 30 in the calibration gas 20 for comparison against the corresponding values measured by the measurement device 23. The calculations can be made on both a wet and dry gas basis. The "dry" concentration calculations, as referred to herein, exclude (or factor out) the contribution of water from the humidificant 40 and analyte 30 in increasing the calibration gas 20 volume, which reduces the concentration of the analyte 30 per unit volume of the calibration gas 20.

In some cases, it may be desirable that the apparatus 10 provide a calibration gas 20 that includes a second analyte (not shown in FIG. 1). The second analyte can be provided as an alternative to, or in addition to, the first analyte 30. To provide the second analyte, the carrier gas source 19 can be changed from providing a "zero gas" carrier gas 18 to a carrier gas source 19a that includes an amount of the second analyte. For example, the carrier gas source 19a could be in the form of a standard gas cylinder providing a carrier gas 18 having a known composition of the second analyte. If the carrier gas source 19a can provide the carrier gas stream 18 at a known flow rate, the mass flow controller 70 can be omitted. The carrier gas source 19 can be, for example, but not limited to, a saturated vapor source containing elemental mercury at a known concentration for delivery of a known flow rate, or a calibration gas cylinder.

Figure 2:
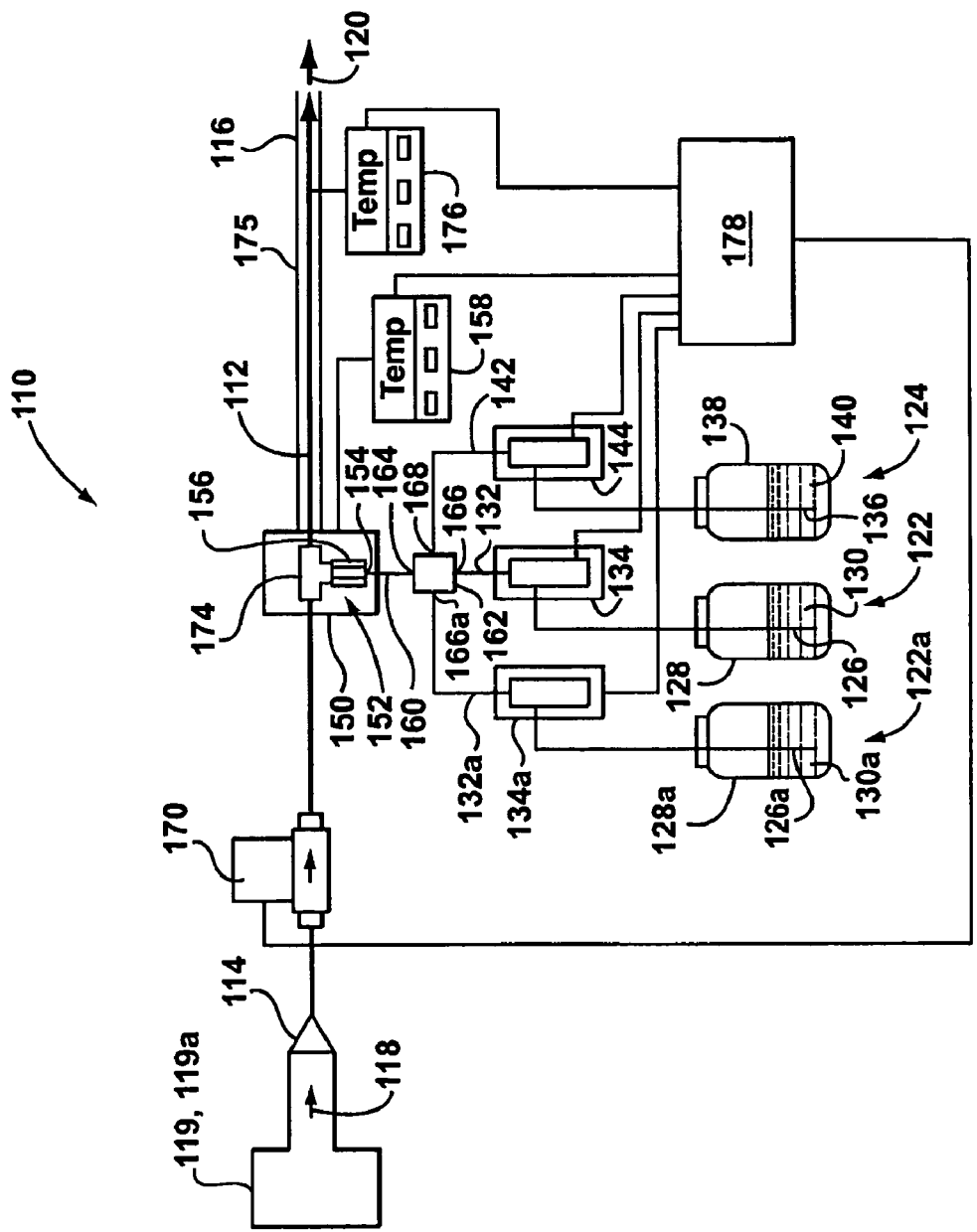
FIG. 2 is a schematic diagram of another embodiment of a calibration gas delivery apparatus in accordance with the present invention.

An alternative calibration gas delivery apparatus 110 in accordance with the present invention is shown in FIG. 2. The apparatus 110 has many similarities to the apparatus 10, and like features are identified by like reference characters, incremented by 100. The apparatus 110 includes a first injection unit 122, a second injection unit 124, and a third injection unit 122a. The third injection unit 122a is adapted to introduce a third component 130a into the calibration gas 120, and has a third intake 126a in fluid communication with a third reservoir 128a.

In the embodiment illustrated, the third component 130a is in the form of a second analyte. The third reservoir 128a is adapted to contain an amount of the second analyte 130a in liquid form. The third injection unit 122a has a third outlet 132a in fluid communication with the delivery conduit 112, and a third flow inducer 134a to facilitate flow of the second analyte 130a from the third intake 126a to the third outlet 132a. The apparatus 110 has a manifold 162 having a third inlet port 166a, in addition to the first and second inlet ports 166, 168, that is connected in fluid communication with the third outlet 132a.

The third flow inducer is, in the embodiment illustrated, similar to, or the same as, the first flow inducer 134. The third flow inducer 134a can be adjusted independently of the first and second flow inducers 134, 144, by, for example, the controller 178. This can allow selective addition of the first and second analytes 130, 130a to the calibration gas 120. Any of the three flow inducers 134, 144, or 134a can also be adjusted to an off position, in which the respective component 130, 140, or 140a is not supplied to the delivery conduit 112 and is absent from the calibration gas 120. By providing for automatic adjustment of each of the three flow inducers 134, 144, and 134a via the controller 178, distinct calibration cycles can be performed automatically, providing for convenient calibration of the measurement device 123 over a wide range of concentrations of the respective components 130, 140 and 130a.

It is to be appreciated that, in accordance with the present invention, further additional injection units 122b, 122c . . . (etc.) can be provided with the apparatus 110. The additional injection units can be controlled by the controller 178, and can introduce other respective analytes into the calibration gas 120. The apparatus 110 can thus conveniently provide a calibration gas 120 that with a variety of components and/or concentrations and with selectively varied levels of humidification. The humidificant 140 can be included or omitted as required; for some applications, adequate humidification may be provided by the liquid solvents of the analyte(s) and/or be included in the carrier gas 118. The calibration gas 120 can also be configured to closely match the nature of the actual emission gas being monitored by the device 123, by selecting components for the respective injection units that match components known to exist in the emission gas.

Figure 3:
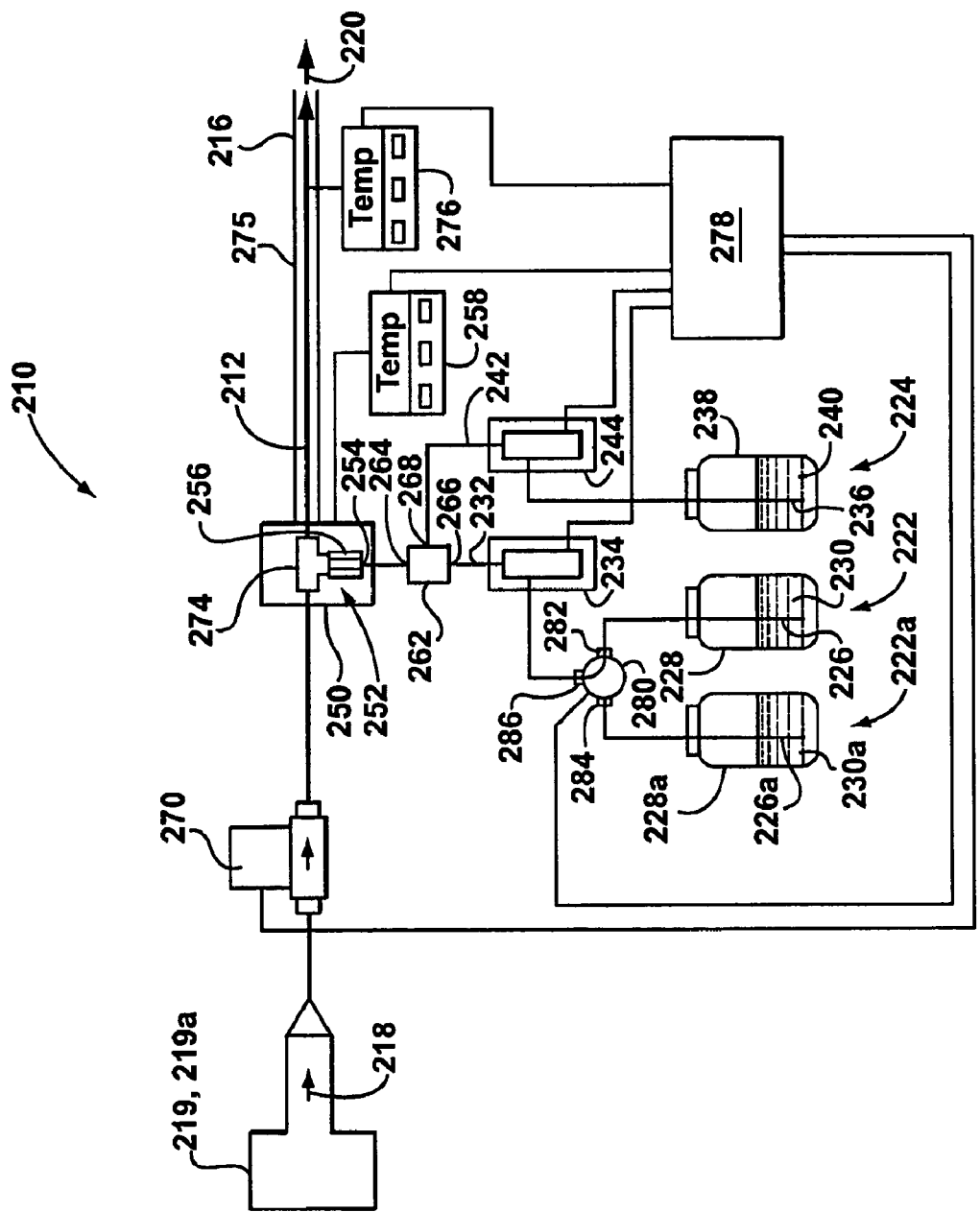
FIG. 3 is a schematic diagram of a further embodiment of a calibration gas delivery apparatus in accordance with the present invention.

Another alternative calibration gas delivery apparatus 210 in accordance with the present invention is shown in FIGS. 1 and 3. The apparatus 210 has many similarities to the apparatus 10, and like features are identified by like reference characters, incremented by 200 from FIG. 1. The apparatus 210 includes a first injection unit 222, a second injection unit 224 and a third injection unit 222a. The first injection unit 222 includes a first reservoir 228, and the third injection unit 222a includes a third reservoir 228a. The third reservoir 228a is adapted to supply a third component 230a for injection into the calibration gas 230. The first injection unit 222 includes a third intake 226a in fluid communication with the third reservoir 228a.

The third component 230a can be, but need not be, a third analyte for measurement by, and calibration of, the measurement device 223. The third component 230a can be an agent for otherwise treating or maintaining the measurement apparatus. In the embodiment illustrated, the third component 230a is in the form of an acidic liquid solution that, when combined in vapor form with the carrier gas 218, can serve to clean and condition members of the measurement system including, for example, the probe 221.

The first injection unit 222 is provided with first and third intakes 226 and 226a that are in selective, adjustable fluid communication with the first outlet 232 via an intake valve 280. The intake valve 280 can provide adjustment of the relative amount of the first and third components 230, 230a to be introduced into the calibration gas 220.

In the embodiment illustrated, the intake valve 280 is a three-port, two-position valve. The valve 280 has a first valve inlet 282 in fluid communication with the first intake 226 of the first injection unit 222. The valve 280 has a second intake 284 in fluid communication with the third intake 226a of the first injection unit 222. The valve 280 has a valve outlet 286 in fluid communication with the flow path 252 of the vaporizer 250.

When the intake valve 280 is in the first valve position, the valve outlet 286 is in fluid communication with the first valve inlet 282 and isolated from the second valve inlet 284, for drawing an amount of the first analyte 230. When the intake valve 280 is in the second valve position, the valve outlet 286 is in fluid communication with the second valve inlet 284, and is isolated from the first valve inlet 282, for drawing an amount of the third component 230a.

By changing the position of the valve (from the first to the second valve positions and back again), the first and third components 230, 230a, respectively, can alternatively be introduced into the calibration gas 220. Where the third component 230a is, as in the illustrated embodiment, formed of a cleaning solution, the valve 280 can be moved from the first position to the second position to perform a periodic cleaning cycle. The valve 280 can be electronically controlled, and can be moved between the first and second positions by the controller 278. Periodic cleaning can thus be conducted automatically at regularly scheduled (i.e. programmed) intervals. The cleaning step can be conducted shortly prior to the actual measurement of the calibration gas by the device 123 to enhance the accuracy and repeatability of the overall calibration procedure.

While techniques are known for generating and supplying calibration gases for calibration of various types of measuring equipment, a common characteristic of known systems is simply to provide an analyte of interest in a desired concentration in a carrier gas; no attempt is made to replicate the general characteristics of the sample gas usually sampled and measured by the measuring equipment. Correspondingly, it has not been realized that, in the detection of some analytes, the characteristics of the calibration gas stream can strongly influence the ability of the measuring equipment to transport said calibration gases.

This characteristic is evident when: the analyte to be detected may only be present at extremely low levels; the analyte has a strong tendency to react with materials present or be absorbed on available surfaces; the usual gas environment is complex and includes various materials, e.g. fly ash and other particulates, that can promote such reaction of absorption. All these features are usually found in the detection of mercury in stack gases.

Accordingly what the present inventors have realized is that the calibration gas, with an entrained analyte should simulate the gas usually sampled, to the extent necessary to prevent the occurrence of the effects listed in the preceding paragraph. Thus, for mercury detection, and in particular for the detection of ionic mercury, one needs to be aware that the environment in a flue stack includes deposited fly ash conducive to causing mercury to absorb or deposit on it; and the actual flue gas is usually a complex and acidic matrix that strongly effects the behaviour of the mercury. Thus any significant change in the composition of the gas flowing through the flue stack can significantly alter the behaviour of the mercury. This is commonly handled by running existing calibration equipment for a long enough time for a steady state to be reached; for example if the use of a dry gas promoted deposition of mercury, then the calibration is run for a long enough time for sufficient mercury to be deposited that a steady state is reached where there is no net additional deposition and all the mercury as the analyte in the calibration gas passes through to the measuring equipment. However, in many cases the time required is too long and is not acceptable.

Accordingly the present invention provides a method and apparatus intended to overcome, or at least mitigate these problems. To achieve this, a number of variations in the described embodiments are within the scope of the present invention.

For the carrier gas supplied, this could comprise a combination of two or more gases, either supplied separately and mixed by the apparatus of the present invention, or supplied in an already mixed form. Additionally, one or more the supplied gases can include one or more analytes of interest at a desired concentration. For example one of the gas sources, or the only gas source, can be an elemental mercury source, such as the Tekran® Model 3310 CEM Mercury Calibrator, that serve to supply simultaneously a desired gas and an analyte. Any other conventional calibration gas generator can be used, with the basic requirement being that it produces a known concentration of analyte; it can also be such as to measure or regulate the flow rate of the gas/analyte mixture, or if this feature is not present, mass flow regulation can be provided by the apparatus of the present invention.

The number of analyte sources provided can vary. At a minimum, if the gas source also provides the analyte of interest, e.g. an elemental mercury source, then it may only be necessary to supply humidificant to the gas flow, i.e. there would be no separate supply of an analyte solution. Otherwise, there can be one, two or more separate supplies of analyte in solution. Each of these can include one or more analytes, and in each case, the solvent can be simple single solvent or it can be a mixture.

The humidificant supply may not always be needed. The concept is that any analyte in solution will provide a base level of humidification, the characteristics of which will depend on the solvent and the concentration of the analyte in the solution. (Commonly gases provided in compressed state in a cylinder are essentially dry). Then, as required, additional humidification is added to give the calibration gas a desired level of humidification, both in terms of relative humidity level(s) and also in terms of the humidificants used. These can include, in addition to water, various acids that simulate the properties of usual sample gases.

Where the apparatus and method are used to supply mercury for calibration, typically levels are 0.05-200 $\mu g/m^3$ both elemental and ionic mercury, but note that measuring equipment being calibrated may be capable of measuring to much higher levels, e.g. 5000 $\mu g/m^3$ and hence may need to be calibrated at that level. For the humidity level, this should usually correspond to that found in a stack, e.g. 6-10%, and more generally a humidity level in the range 1-30% could be used. Also, it is envisaged that the present invention can be used to clean the probe 21 by providing a high level of humidity, e.g. 100%, without any analyte.

It is to be understood that what has been described are preferred embodiments of the invention. The invention nonetheless is amenable to certain changes and alternative embodiments without departing from the subject invention, the scope of which is defined in the following claims.

The invention claimed is:

1. A calibration gas delivery apparatus for delivering a selectively humidified calibration gas to a measurement probe, the apparatus comprising:
   a) a delivery conduit having a conduit inlet adapted to receive a carrier gas stream and a conduit outlet for delivering a calibration gas stream;

b) a mass flow controller in the delivery conduit for controlling the flow of the carrier gas;
c) a first injection unit having a first intake in fluid communication with a first reservoir and a first outlet in fluid communication with the delivery conduit, the first reservoir adapted to hold an ionic mercury solution, the first injection unit delivering the ionic mercury solution at a known flow rate in liquid form;
d) a second injection unit having a second intake in fluid communication with a second reservoir and a second outlet in fluid communication with the delivery conduit, the second reservoir adapted to hold water as a humidificant, the second injection unit delivering the water at a known flow rate; and
e) at least one vaporizer downstream of the first and second outlets and upstream of the conduit outlet for converting the ionic mercury solution and the water into vapor form and delivering a calibration gas including the carrier gas, ionic mercury, and water vapor to the conduit outlet, whereby the concentrations of the ionic mercury and water in the carrier gas are known.

2. The apparatus of claim 1 further including respective first and second flow inducers for drawing fluid from the first and second reservoirs and providing precise amounts of the first analyte and humidificant liquids to the first and second outlets, respectively.

3. The apparatus of claim 2 wherein each of the first and second injection units is selectively adjustable to adjust the amounts of the first analyte and humidifcant liquids being delivered to the respective first and second outlets.

4. The apparatus of claim 2 wherein each of the first and second flow inducers comprises a precision displacement pump.

5. A calibration gas delivery apparatus for delivering a selectively humidified calibration gas to a measurement probe, the apparatus comprising:
a) a delivery conduit having a conduit inlet adapted to receive a carrier gas stream and a conduit outlet for delivering a calibration gas stream;
b) a mass flow controller in the delivery conduit for controlling the flow of the carrier gas;
c) a first injection unit having a first intake in fluid communication with a first reservoir and a first outlet in fluid communication with the delivery conduit, the first reservoir adapted to hold an ionic mercury solution, the first injection unit delivering the ionic mercury solution at a known flow rate in liquid form;
d) a second injection unit having a second intake in fluid communication with a second reservoir and a second outlet in fluid communication with the delivery conduit, the second reservoir adapted to hold water as a humidificant, the second injection unit delivering the water at a known flow rate;
e) a manifold having first and second inlet ports connected to the first and second outlets, respectively, of the first and second injection units, and an exhaust port;
f) a vaporizer in the delivery conduit and connected to the manifold exhaust port and including a heater for converting the ionic mercury solution and the water into vapor form and for delivering a calibration gas including the carrier gas, analyte vapor, and humidificant vapor to the conduit outlet, whereby the concentrations of the ionic mercury and the water in the carrier gas are known.

6. The apparatus of claim 1, including at least one additional injection unit and a corresponding additional reservoir for at least one of an additional analyte and an additional humidificant, for delivering said at least one of an additional analyte and an additional humdificant at a known flow rate.

7. The apparatus of claim 6, further including a valve connected to at least two of the injection units for switching therebetween.

8. The apparatus of claim 1, wherein the conduit inlet is adapted to receive at least two carrier gas streams.

9. A calibration gas delivery apparatus for delivering a selectively humidified calibration gas to a measurement probe, the apparatus comprising:
a) a delivery conduit having a conduit inlet adapted to receive at least one carrier gas stream including an analyte and a conduit outlet for delivering a calibration gas stream at a known flow rate;
b) an injection unit having an intake in fluid communication with a reservoir and an outlet in fluid communication with the delivery conduit, the reservoir adapted to hold a water, the injection unit delivering the water at a known flow rate;
c) at least one vaporizer downstream of the outlet and upstream of the conduit outlet for converting the water to vapor form and delivering a calibration gas including all of said at least one carrier gas and water vapor to the conduit outlet, whereby the concentration of the water vapour in the carrier gas stream is known;
d) an elemental mercury source that provides the carrier gas stream with elemental mercury entrained therein, wherein the conduit inlet is in fluid communication with the elemental mercury source, and the elemental mercury is provided at a known flow rate, whereby the concentration of the elemental mercury in the carrier gas stream is known.

10. A calibration gas delivery apparatus for delivering a selectively humidified calibration gas including mercury chloride to a measurement probe, the apparatus comprising,
(a) a delivery conduit having a conduit inlet adapted to receive a carrier gas stream and a conduit outlet for delivering a calibration gas stream;
(b) a mass flow controller in the delivery conduit for controlling the flow of the carrier gas;
(c) a first injection unit having a first intake in fluid communication with a first reservoir and a first outlet in fluid communication with the delivery conduit, the first reservoir holding a liquid mercury chloride solution and the first injection unit delivering the mercury chloride solution at a known flow rate;
(d) a second injection unit having a second intake in fluid communication with a second reservoir and a second outlet in fluid communication with a delivery conduit, the second reservoir adapted to hold (a water, the second injection unit delivering the water at a known flow rate; and
(e) at least one vaporizer downstream of the first and the second outlets and upstream of the conduit for converting the mercury chloride solution and the water to vapour form and delivering a calibration gas including the carrier gas, mercury chloride vapour and water vapour to the conduit outlet, with known concentrations of water vapor and mercury chloride.

11. A calibration gas delivery apparatus for delivering a selectively humidified calibration gas to a measurement probe, the apparatus comprising:
a) a delivery conduit having a conduit inlet adapted to receive a carrier gas stream and a conduit outlet for delivering a calibration gas stream;
b) a mass flow controller in the delivery conduit for controlling the flow of the carrier gas;

c) a first injection unit having a first intake in fluid communication with a first reservoir and a first outlet in fluid communication with the delivery conduit, the first reservoir adapted to hold a first analyte in liquid form and the first injection unit delivering the analyte at a known flow rate;

d) a second injection unit having a second intake in fluid communication with a second reservoir and a second outlet in fluid communication with the delivery conduit, the second reservoir adapted to hold a water and to deliver the water at a know flow rate;

e) a manifold having first and second inlet ports connected to the first and second outlets, respectively, of the first and second injection units, and an exhaust port;

f) a vaporizer in the delivery conduit and connected to the manifold exhaust port and including a heater for converting the analyte and the water to vapor form and for delivering a calibration gas including the carrier gas, analyte vapor, and water vapor to the conduit outlet, wherein the vaporizer is connected to a T fitting in the delivery conduit, whereby the analyte and the humidificant liquids are heated prior to being supplied to the delivery conduit, and whereby the concentrations of the analyte and water vapor in the carrier gas stream are known.

12. An apparatus is claimed in claim 11, including a heater for the delivery conduit downstream from the T fitting.

* * * * *